United States Patent [19]

Kortas

[11] Patent Number: 4,930,075

[45] Date of Patent: May 29, 1990

[54] TECHNIQUE TO EVALUATE MYOCARDIAL ISCHEMIA FROM ECG PARAMETERS

[75] Inventor: Ricardo G. Kortas, Stanford, Calif.

[73] Assignee: The Board of Trustees of The Leland Stanford Junior University, Stanford, Calif.

[21] Appl. No.: 221,798

[22] Filed: Jun. 6, 1988

Related U.S. Application Data

[63] Continuation of Ser. No. 73,335, Jul. 13, 1987, abandoned, which is a continuation of Ser. No. 646,224, Aug. 30, 1984, abandoned.

[51] Int. Cl.$^5$ ............................................. A61B 5/04
[52] U.S. Cl. ............................... 364/413.06; 128/703
[58] Field of Search ...................... 364/413.06, 413.05, 364/413.01; 435/637, 17; 128/702, 711, 904, 700, 703

[56] References Cited

U.S. PATENT DOCUMENTS

| | | | |
|---|---|---|---|
| 4,173,971 | 11/1979 | Karz | 128/702 |
| 4,419,999 | 12/1983 | May, Jr. et al. | 128/736 |
| 4,492,753 | 1/1985 | Shell et al. | 128/637 X |

*Primary Examiner*—Joseph Ruggiero
*Assistant Examiner*—Charles B. Meyer
*Attorney, Agent, or Firm*—Flehr, Hohbach, Test, Albritton & Herbert

[57] ABSTRACT

As a method of diagnosing ischemia non-invasively, the effective component of the ST-segment depression (STe) of an electrocardiogram is measured. A precise mathematical relationship between the values of the ST-segment depression, slope, and length of the ST-segment was defined and implemented, making it possible to compare any ST-segment morphology against a standard reference of horizontal depression.

12 Claims, 5 Drawing Sheets

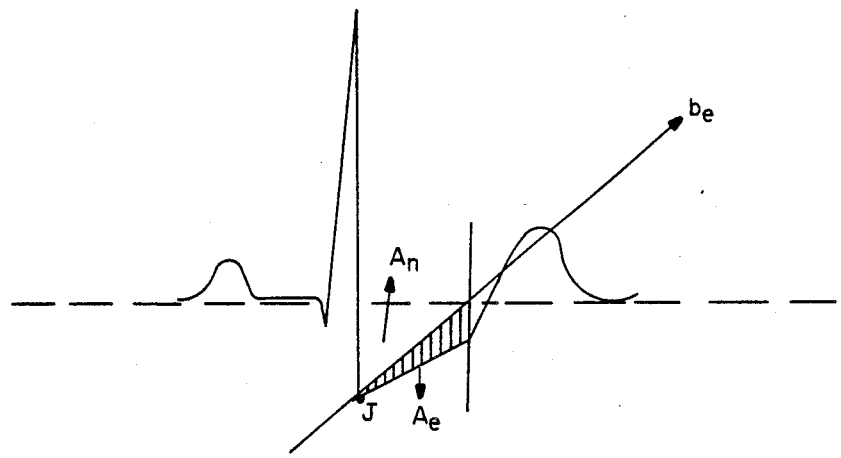
FIG.—1
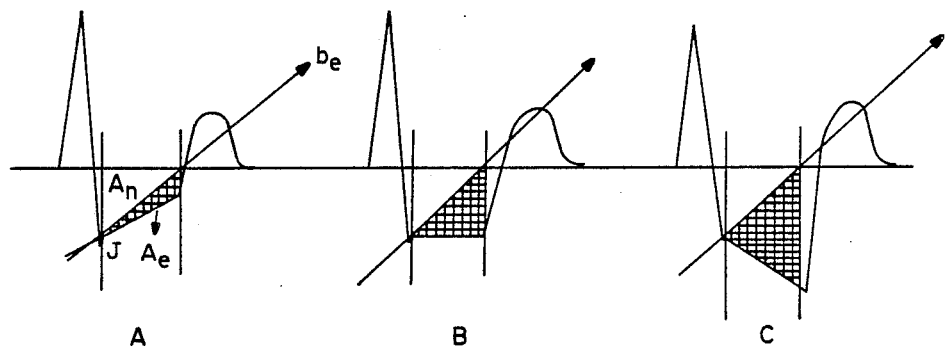
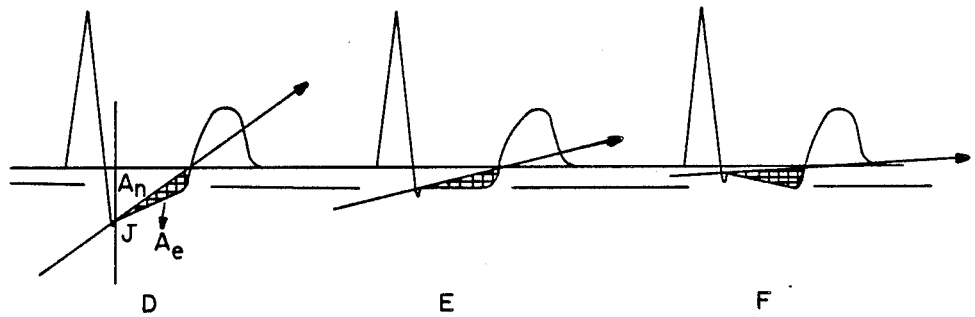
FIG.—2

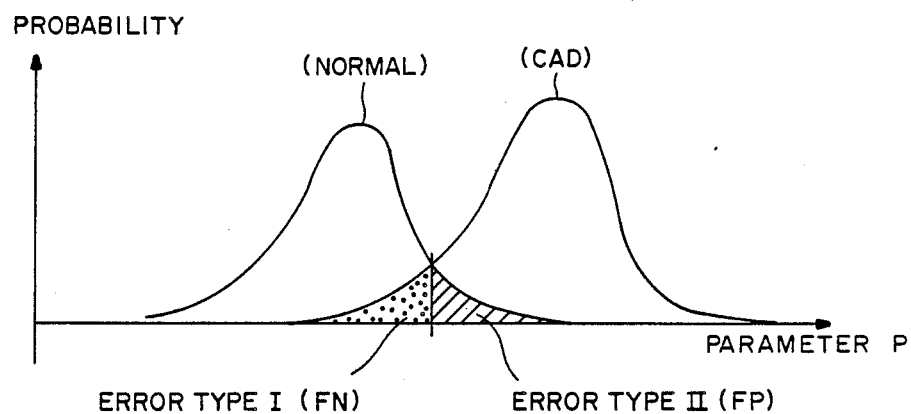
FIG.—3
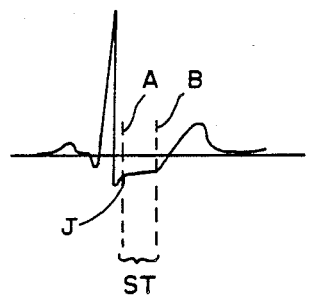
FIG.—4A
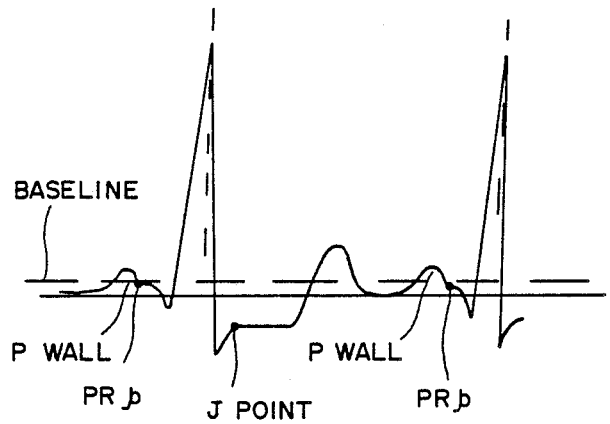
FIG.—4B

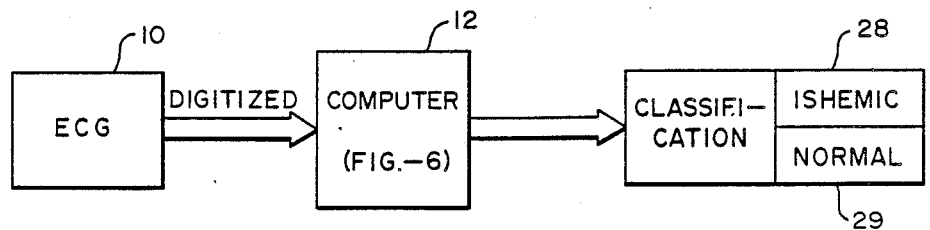
FIG.—5
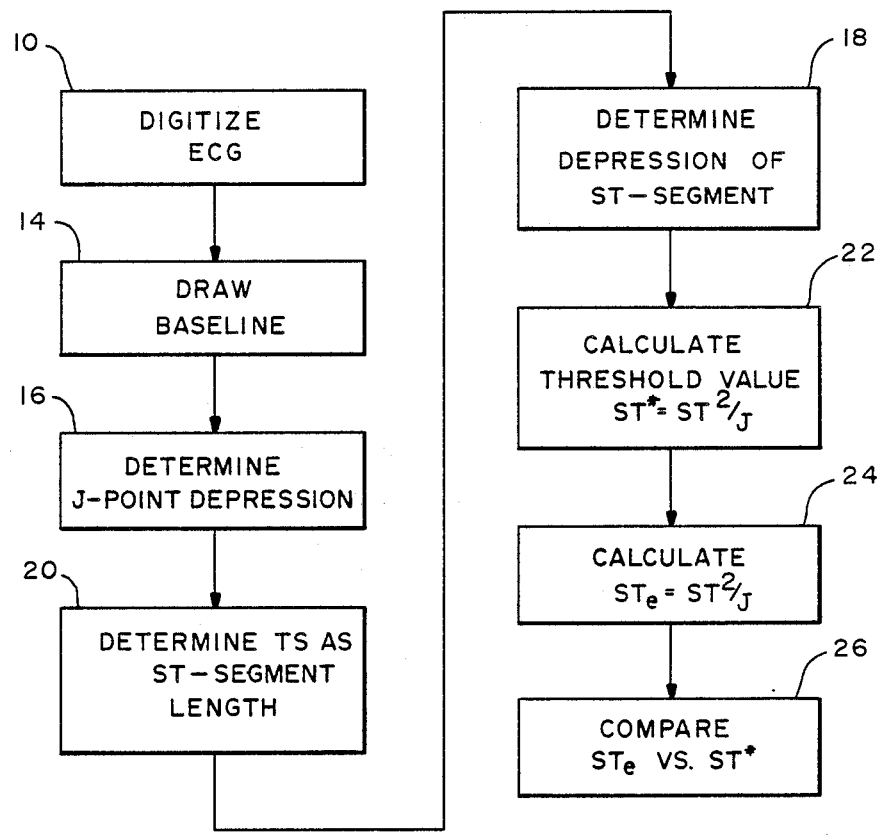
FIG.—6

TECHNIQUE TO EVALUATE MYOCARDIAL ISCHEMIA FROM ECG PARAMETERS

This is a continuation, of application Ser. No. 073,335 filed July 13, 1987, abandoned which was a continuation of application Ser. No. 646,224, filed August 30, 1984.

FIELD OF THE INVENTION

The present invention relates generally to method of non-invasive diagnosis of ischemia and more particularly to a software implemented method of analysis of the ST-segment of an electrocardiogram.

BACKGROUND OF THE INVENTION

The performance of such testing has improved thanks to the increase of the work load, use of computerized analysis, and use of multivariate discriminant analysis.

Nevertheless, the problem of interpreting the significance of the ST-segment depression with upsloping morphology has remained unsolved. It is accepted that the upsloping morphology represents a transition between the physiological depression of the J-point and the "ischemic" morphologies, represented by 1 or more mm of horizontal or downsloping depression, measured at 80 msec after the J-point.

Different criteria has been proposed to cope with different-combinations of the depression and slope, but none was described by a closed mathematical expression, derived exclusively from theoretical properties of the ST-segment.

Three basic problems with the ST-segment analysis had to be solved:

(1) lack of a criterion to express the equivalence between different morphologies.
(2) need to explain the unreliable behavior of the ST-segment integral (area) (Sheffield's index).
(3) need to create a theoretical background for the ST-segment analysis.

SUMMARY OF THE INVENTION

It is an objective of the present invention to provide an improved approach to ST-segment analysis.

It is a further objective of this invention to provide a consistent basis for interpretation of the ST-segment of an ECG.

Since the publication of the study done by Blackburn in 1968, comparing the performance of independent ECG readers, it has been accepted that the lack of a criterion for the interpretation of upsloping morphology is the main source of errors and disagreement in the treadmill interpretation.

The ST-segment area has gained widespread use as an indicator of ischemia. See Sheffield, LT., *Survey of Exercise ECG Analysis Methods*, in van Bemmel, J. H., and Willems, J. L., eds. "Trends in Computer Processed Electrocardiograms" North Holland Publ., 1977: 373–382. Surprisingly, the behavior of this index as presently interpreted is not reliable, sometimes behaving in harmony with clinical knowledge, sometimes not.

Since the introduction of the stress test in 1928, it has always been accepted that the dpression of the ST-segment should be measured against the isoelectric level of the electrocardiogram (ECG), represented by the PR interval, or by the TQ interval.

The fact that depression of the initial part of the ST-segment can be normal (effect of the Ta-wave) creates a logical conflict in the standard ST-segment interpretation, which can be expressed as:

if the J-point depression is normal
and, since the depression does not return to the isoelectric level instantaneously,
then a certain amount of depression should also be considered normal during the period of time used by the signal to return to the isoelectric level.

The use of the isoelectric level of the ECG signal as the baseline (reference) becomes inappropriate whenever the J-point is depressed. To overcome this problem, an entirely new method of interpreting the ST-segment region has been developed. As a first step, FIG. 1 shows a new baseline (effective baseline, or $b_e$) newly defined as part of the development of the method of the present invention. This effective baseline $b_e$ extends from the J-point to the point of the isoelectric level corresponding to the "end" of the ST-segment. The "end" is defined as the point where the slope becomes much steeper, i.e., the transition between the ST-segment and the T-wave. This effective baseline $b_e$ represents the theoretical, average pattern followed in returning from the J-point to the isoelectric level.

FIG. 1 also shows the effect of the effective baseline upon the ST-segment area: it divides the area into two components, one normal ($A_n$), and one potentially related to coronary disease CAD ($A_e$). The parameters used for the calculations are:

ts: length of the ST-segment expressed in millimeters (for example, 80 msec will correspond to ts=2 mm using standard paper speed of 25 mm/sec.)

J: depression of the J-point in millimeters

ST: depression of the ST-segment measured at the "end"

FIG. 2 shows the effect of changing the morphology of the ST-segment upon the ST-area and also illustrastes why the present method more accurately interprets the ST-region. Using the morphology of FIG. 2A as a reference, we can see if the behavior of the ST-area is in harmony with the clinical knowledge; for example, FIG. 2B is clinically more significant than FIG. 2A and it also has a larger ST-area; the same is true of FIG. 2C. The reason for this is readily apparent when the effective baseline is drawn. For this sequence, it is the increase in area $A_e$ which indicates ischemia.

In FIGS. 2E and 2F the total area A is reduced, as compared to the area in FIG. 2D which classically according to Sheffield's criteria referenced above should indicate that there is a lower probability of ischemia; in fact, experience dictates that ischemia is more probable in these cases. Again, when the effective baseline is drawn, in accord with this invention, it can be seen that the change in total area is due to a reduction in area $A_n$, thus again indicating likely ischemia. Therefore, we can conclude that if the change of the ST-area is a result of a change in the $A_e$ component, then the change will be in harmony with clinical experience. On the other hand, if the change is a result of a change in the $A_n$ component, the variation of the ST-area will be in conflict with accepted interpretations.

Thus, according to the present invention, to provide a method of interpretation which is more accurate than known in the prior art, interpretation of the ECG proceeds on the basis that an effective baseline $b_e$ can be drawn dividing the ST-segment area into two regions, $A_n$ and $A_e$. Region $A_e$ contains most of the information useful in detecting ischemic morphologies, but $A_n$ also contains useful information. According to a preferred embodiment of the invention, a ratio of $A_e/A_n$ is developed; if compared to a threshold value which is a function of the length of the ST-segment, then probable ischemic morphology can be detected. More specifically, if the threshold is calculated using the formula $ST^*=2/ts$, where ts is the horizontal travel of the ST-segment in mm.; and $ST_e$ (effective component of ST depression)=$ST^2/J$, where ST is the vertical distance from the end of the ST-segment to the baseline, and J is the J-point depression; then where $ST_e \geq ST^*$, ischemia is indicated.

BRIEF DESCRIPTION OF THE DRAWINGS

A mathematical derivation demonstrating the effectiveness of this analysis, as well as a pseudocode description of the sequence of the analysis to be undertaken follows. Reference should be made to the attached drawings in which:

FIGS. 1 and 4b show certain essential features of an electrocardiogram useful in understanding the invention;

FIG. 2 illustrates different potential ST-segments, some of which could not be successfully analyzed using known techniques;

FIG. 3 is a statistical model useful in understanding the mathematical derivation which follows;

FIGS. 4a and 4b label essential elements of an electrocardiogram useful in understanding the method of analysis of this invention;

FIG. 5 is a schematic of the necessary hardware to implement the invention;

FIG. 6 is a flow chart of the software to implement the invention.

DETAILED DESCRIPTION OF A PREFERRED EMBODIMENT

The key issue in this analysis is the correct classification of a patient in one of two categories, normal or ischemic.

Whenever a decision has to be made (according to classical decision making theory), in order to classify a new individual in one of two categories, the following steps are normally taken:
(1) selection of a reliable parameter (p) to be used in the analysis.
(2) determination of the optimum threshold (p*), which will allow discrimination between the two categories.

Step #1 comes from experience in that particular field under study, e.g., here, myorcardial ischemia, which allows the selection of a parameter correlated to the categories. Step #2 is most frequently obtained by looking for the value of p that minimizes the sum of potential errors.

For that particular case of diagnosing disease, these errors are called False Negative and False positive.
Sum of errors=FN+FP=False Negatives+False Positives In order to estimate p* it has always been necessary to study the behavior of the parameter p in large populations of individuals, and then identify p* from the plotted probability density functions, like the illustration in FIG. 3.

What follows next is a method to estimate p* without any information about the probability density functions of the categories. While the traditional approach requires the collection of large amount of data in order to plot the density functions, and then find a value for p* which compromises between the conflicting natures of the two categories, the present method uses as its source of information the conflicting natures of the components of the parameter.

From FIG. 1 we have that:

$$A_n=(ts.J)/2 \text{ and, } A_n^{-1}=(2/ts.J)$$

$$A_e=(ts.ST)/2 \text{ and, } A_e^{-1}=(2/ts.ST)$$

The estimation of ST* became possible by minimizing a discriminant function defined as:

$$\Sigma \text{errors}=(A_e+A_n^{-1})+(A_n+A_e^{-1})$$

The arithmetic expressions $(A_e+A_n^{-1})$ and $(A_n+A_e^{-1})$ have a behavior similar to the FN and FP components of the statistical discriminant function Sum of errors because:
(1) They have a "scale-like" behavior, with one going up (increases) when the other goes down (decreases).
(2) The first is related to the possibility of disease while the second expression is related to the possibility of normality.

For example, if in FIG. 3, ST* (or p*) is moved toward the CAD category, then FN increases and FP decreases. In a similar way, if the ST morphology has a change toward morphologies more strongly related to the CAD category (FIG. 2), then $(A_e+A_n^{-1})$ increases and $(A_n+A_e^{-1})$ decreases.

$$\Sigma \text{errors} = (A_e + A_n^{-1}) + (A_n + A_e^{-1}) =$$

$$\left( \frac{ts}{2} \cdot ST + \frac{2}{ts} \cdot \frac{1}{J} \right) + \left( \frac{ts}{2} \cdot J + \frac{2}{ts} \cdot \frac{1}{ST} \right) =$$

$$\left( \frac{ts^2 \cdot ST \cdot J + 4}{2ts \cdot J} \right) + \left( \frac{ts^2 \cdot ST \cdot J + 4}{2ts \cdot ST} \right)$$

Finding the partial derivatives in order to minimize the sum of errors:

$$(1) \quad \frac{d(\Sigma \text{errors})}{dST} = \frac{ts}{2} + \frac{2ts^3 \cdot ST \cdot J - 2ts^3 \cdot ST \cdot J - 8ts}{(2ts \cdot ST)^2}$$

$$= \frac{ts}{2} - \frac{2}{ts \cdot ST^2}$$

Making the derivative equal to zero, results in:

$$\frac{ts}{2} = \frac{2}{ts \cdot ST^{*2}}, \text{ or } ST^* = \frac{2}{ts} \qquad (I)$$

$$(2) \quad \frac{d(\Sigma \text{errors})}{dJ} =$$

$$\frac{(ts^2 \cdot ST) \cdot (2ts \cdot J) - (ts^2 \cdot ST \cdot J \cdot +4) \cdot (2ts)}{(2ts \cdot J)^2} +$$

$$\frac{ts}{2} = \frac{-2}{ts \cdot J^2} + \frac{ts}{2}$$

Making the derivative equal to zero, results in:

$$(2/ts.J^{*2})=ts/2, \text{ or } J^*=2/ts \qquad (II)$$

(3) $\frac{d(\Sigma errors)}{dts} \rightarrow$ after making equal to zero, results in:

$$ts^* = \frac{2}{\sqrt{ST \cdot J}},$$

which is redundant (can be obtained from equations (I) and (II))

CONCLUSION

From equations (I) and (II) we see that the ST-segment morphology corresponding to the optimum threshold satisfies the conditions:

$$ST^* = J^* = 2/ts \quad \text{(III)}$$

that means that ST* has horizontal morphology with a depression of 2/ts millimeters. It is interesting to note that the value selected by the clinical experience (1 mm of horizontal depression) is indeed the optimum threshold when the depression is measured at 80 msec the J-point (ts=2 mm).

From equations and definitions presented previously, we have that:

$$\frac{A_e}{A_n} = \frac{(A_e + A_n^{-1})}{(A_n + A_e^{-1})} = \frac{ST}{J} \quad \text{(IV)}$$

\*\*\* so whenever the ST-segment morphology changes, it changes the balance (ratio) between $A_e$ and $A_n$, and consequently it changes the balance between the probability of being a FP or a FN.

Equation (IV) shows that the horizontal morphologies are well balanced, with ST=J and $A_e/A_n=1$ (it is no surprise that horizontal morphologies are the most reliable and widely used). If the morphology is upsloping, then:

$$ST < J, \text{ and } A_e/A_n < 1.$$

This result explain why for the same amount of ST depression, an upsloping morphology is less clinically significant than a horizontal.

Defining the (ST/J) value as "gain", then it becomes possible to transform any ST morphology into its equivalent horizontal. The effective (or, equivalent) horizontal depression will be:

$$STe = (ST/J) \cdot ST$$

or, $$STe = ST^2/J \quad \text{(V)}$$

Note: it is clear that any horizontal morphology will have a horizontal equivalent equal to itself, because ST/J will be equal to 1.

SUMMARY

Two equations were derived:

(1) $St^* = 2/ts \ (=J^*)$ which calculates the optimum discriminant threshold for choosing between probable or non-probable ischemia as a function of the length of the ST-segment (and consequently, as a function of the QT-interval).

(2) $STe = ST^2/J$ which calculates the horizontal depression equivalent to the given morphology. "Equivalent" means having the same clinical significance when the balance (ratio) between $A_n$ and $A_e$ is taken into account.

Classification Criterion:

if STe ≧ ST* then the morphology should be labeled "ischemic".

An outline of a software driven approach to this analysis follows with reference to FIGS. 5 and 6. The method could obviously be implemented by digitizing the ECG (FIG. 5), and then analyzing the ST-segment thereof in a computer 12 using the following sequence:

THE EFFECTIVE COMPONENT OF THE ST-SEGMENT ANALYSIS a general description using pseudocode

```
program DRIVER;
    (* arbitrary main program making use of the
    technique *)
begin
    for (every identified heart beat) do
    BASELINE; (* draw the baseline *)
    J-POINT (J);
    (* returns the amount of J-point depression *)
    ST-END (ST,ts);
    (* returns the amount of depression at the end of the
    ST segment, and also the length of the ST-segment *)
    STe (J,ST,ts,ST*,STe);  (* returns ST* and STe *)
    if (26) (STe > = ST*)
    then label (28) the heart beat as "ischemic"
    else label (29) the heart beat as "normal";
    end-for;
end.
procedure BASELINE (14);
begin
    from the fiducial point, move backwards until the PR-b
    point is found;
    repeat this step for the next beat, finding its PR-b
    point;
    draw the baseline passing through these two points;
end;
>>> Note:  PR-b is defined as the point where the slope
            of the PR interval changes, and it is preceded
            by a wave being a sequence of samples with a
            maximum or minimum value, and a duration
            smaller than 120 msec.
procedure J-POINT (J);
begin
    from the fiducial point, move forwards, first identi-
    fying the S-wave (point of minimum value), and then
    identifying the J-point as the first point where the
    ST-slope changes, after the S-wave;
    draw a line passing by the S-point and orthogonal to
    the baseline; the intersection of these two lines
    defines the point labeled "A"; (* see FIG. 4a*)
    the value of the J parameter is the distance from the
    J-point to the A point (16);
    return the value of J;
end.
procedure ST-END (ST,ts);
begin
    from the J-point, move forwards until the ST-segment
    slope changes, or the point considered as the end of
    the ST-segment;
    draw a line through the ST-end point, orthogonal to
    the baseline. The intersection of these two lines
    defines the point label as "B";
```

-continued
```
            the value of the ST parameter is the distance from the
            ST-end point to the B point (18);
            the value of the ts parameter is the distance between
            A and B (20);
    end
    procedure ST-e (J,ST,ts, ST*, STe);
    begin
            if (the J parameter is very small, i.e. smaller than
            0.1 mm) (* avoid division by 0 *)
                    then if (the ST parameter is very small)
                            then begin
                                    STe = 0;
                                    go to "next"
                            end;
                    else
                            add to J the value of a constant obtained from
                            the Noise-table;
            STe = ST²/J (22);
    next:
            ST* = 2/ts (24);
    end.
```

Notes:

(1) The Noise-table contains a group of constants, calculated for different values of SNR (signal-to-noise ratio); these constants are very small, small enough not to disturb the calculation of STe for regular values of ST and J, but at the same time, big enough to offset the effect of noise which produces false ST-point depression. Noise at the J-point is not significant; but noise at the ST point, when in fact there is no depression at all, should be discounted, and can be done by observation.

(2) When avoiding the division 0/0, the parameter STe assumed the value zero because that is the value of the limit of ST/J when both go to zero (with $ST \neq J$). For the case where ST=J, then the limit will be equal to 1.

(3) The previous description of the basic characteristics of the method shows that there are numerous variations of the procedures used to support the final STe calculation.

For example:

The new method may be limited to just removing the $A_n$ component from the Sheffield-area (integral) i.e. the complete area defined by the ST-segment and isoelectric baseline.

The method may include the transition between the ST-segment and the T-wave in the evaluation of the ST-end point Higher-order polynomials may be used to draw the effective baseline, or even an exponential function.

Different combinations of $A_n$ and $A_e$ may be used in order to create the two arithmetic expressions (example: $A_n^2 + (A_e^{-1})^2$ and $A_e^2 + (A_n^{-1})^2$).

A single value of STe, instead of area, or a combination of individual values may be used by drawing a single vertical line from the isoelectric baseline to the ST-segment, and using the values above and below the effective baseline as the two parameters equivalent to $A_n$ and $A_e$.

Alternatively, (although probably less accurately), the difference between $A_e$ and $A_n$ may be used instead of the ratio of $A_e/A_n$ to develop the value of $ST_e$. In this instance, instead of $$ST_e = ST \cdot \frac{A_e}{A_n},$$

we would use $$ST_e = ST + (A_e - A_n)$$
$$= ST + \left(\frac{ts}{2} ST - \frac{ts}{2} J\right)$$

$$STe + ST\left(1 + \frac{ts}{2}\right) - J\left(\frac{ts}{2}\right)$$

then our definition of gain$=A_e-A_n$ and, our definition of $STe = ST + (A_e - A_n)$ The STe parameter may be mixed with other physiological parameters in order to create a different and final index of ischemia.

Variations may occur in the support procedures, i.e small variations in the drawing of the baseline, in the definition of the J and ST-point values, or even fixing the value of ts (ST-segment length) as equal to 80 msec.

Therefore the present invention should be limited only by the following claims.

What is claimed is:

1. A method of evaluating a patient for ischemia by evaluation of an electrocardiogram of that patient and specifically an ST segment thereof, comprising the steps of taking an electrocardiogram of the patient, digitizing the electrocardiogram, determine length of said ST segment, estimating a critical threshold value in said electrocardiogram as a function of the length of the ST-segment of said electrocardiogram, calculating a value representing ST-segment depression relative to a fixed baseline based on signal information representing said baseline and said ST-segment to transform signals representing the ST-segment morphology into signals representing an equivalent horizontal morphology, and comparing said signals representing said equivalent horizontal morphology to said threshold value, where morphologies exceeding said threshold are labelled ischemic.

2. A signal processing system for evaluating and assigning a patient to normal or ischemic categories comprising means for generating a digital representation of an electrocardiogram of said patient, means for analyzing said electrocardiogram and calculating a critical threshold value for said electrocardiogram as a function of the length of the ST-segment of said electrocardiogram, means for calculating a value representing ST-segment depression relative to a fixed baseline based on said digitized signal information representing said baseline and said ST-segment to transform signals representing the ST-segment morphology into signals representing an equivalent horizontal morphology, comparison means for comparing said signals representing said horizontal morphology to signals representing said threshold value and assigning said patient to a normal or ischemic classification based on the result of said comparison.

3. A system as in claim 2 wherein said ST-segment is measured extends from a J-point depression to a change in slope of the ST-segment upward toward the electrocardiogram baseline.

4. A system as in claim 2 wherein said means for representing the baseline draw said isoelectric baseline at the horizontal level defined by the point where the slope of an immediately preceding PR interval changes.

5. A system as in claim 4 wherein said end point of said ST-segment is defined as the point removed from the beginning of the ST-segment where the electrocardiogram changes slope.

6. A system as in claim 5 wherein said end point of said ST-segment is defined as the point removed from the beginning of the ST-segment where the electrocardiogram changes slope, thereby excluding the T-portion of the response.

7. A system as in claim 2 wherein said means for transforming signals representing ST-segment morphology comprise means for drawing orthogonal lines from beginning and end points of said ST-segment to an isoelectric baseline of said electrocardiogram to define an ST region, means for drawing an effective baseline from said beginning point of said ST-segment to the junction of the orthogonal from the end point and the isoelectric baseline thereby effectively dividing said ST region into two regions, and means coupled to said comparison means for forming a ratio between said two regions to compare to said threshold.

8. A system as in claim 7 wherein the end point of said ST-segment is defined as the point removed from the beginning of the ST-segment where the electrocardiogram changes slope.

9. A system as in claim 2 wherein the value calculating means automatically insert the value 80 mm or two seconds.

10. A system as in claim 2 wherein the value calculating means define a signal representing the critical threshold value is a function of horizontal displacement of the ST-segment.

11. A system as in claim 2 wherein said threshold value is calculated in said value calculating means as equal to 2/ts, where ts is the horizontal displacement of the ST-segment along the isoelectric baseline of the electrocardiogram.

12. A patient classification system as in claim 2 wherein said digitizing means include means for digitally representing an isoelectric baseline for said ECG, said means for representing horizontal signam morphology using an effective horizontal value comprising 2/ts.

* * * * *

UNITED STATES PATENT AND TRADEMARK OFFICE
CERTIFICATE OF CORRECTION

PATENT NO. : 4,930,075

DATED : May 29, 1990

INVENTOR(S) : Ricardo G. Kortas

It is certified that error appears in the above-identified patent and that said Letters Patent is hereby corrected as shown below:

In the drawing on the title page, block #22, change "ST* = $ST^2/_J$" to --ST = 2/ts--.

FIG 4A on Sheet 2 of 3, labels A and B should point to the intersection with the horizontal line; and FIG 4A on Sheet 2 of 3, change "ST" to --ts--.

FIG 6 on Sheet 3 of 3, block 22, change "ST* = $ST^2/_J$" to --ST = 2/ts--.

Col. 4, line 13, before the second "+", insert --)--.

Col. 5, line 67, change "St" to --ST--.

Col. 8, line 9, change "STe +" to --STe =".

Col. 10, lines 4 and 5, change "80 mm or two seconds" to --80 msec or 2 mm--.

Col. 10, line 19, change "signam" to --signal--.

Signed and Sealed this

First Day of December, 1992

*Attest:*

DOUGLAS B. COMER

*Attesting Officer*  *Acting Commissioner of Patents and Trademarks*